US011344402B2

(12) United States Patent
Perkins et al.

(10) Patent No.: US 11,344,402 B2
(45) Date of Patent: May 31, 2022

(54) BIFURCATING BRANCH MODULAR ILIAC BRANCH DEVICE

(71) Applicant: Medtronic Vascular, Inc., Santa Rosa, CA (US)

(72) Inventors: Keith Perkins, Santa Rosa, CA (US); Travis Rowe, Santa Rosa, CA (US); Mark Stiger, Santa Rosa, CA (US); Mark Young, Santa Rosa, CA (US); Julie Benton, Santa Rosa, CA (US); Steven Claessens, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 2 days.

(21) Appl. No.: 16/855,780

(22) Filed: Apr. 22, 2020

(65) Prior Publication Data
US 2020/0375724 A1 Dec. 3, 2020

Related U.S. Application Data

(60) Provisional application No. 62/855,163, filed on May 31, 2019.

(51) Int. Cl.
*A61F 2/07* (2013.01)
*A61F 2/954* (2013.01)
(Continued)

(52) U.S. Cl.
CPC ............... *A61F 2/07* (2013.01); *A61F 2/856* (2013.01); *A61F 2/954* (2013.01); *A61F 2002/067* (2013.01); *A61F 2210/0014* (2013.01)

(58) Field of Classification Search
CPC .. A61F 2/07; A61F 2/852; A61F 2/856; A61F 2/954
See application file for complete search history.

(56) References Cited

U.S. PATENT DOCUMENTS

2002/0058986 A1* 5/2002 Landau ................ A61F 2/07
623/1.13
2014/0172064 A1 6/2014 Kelly
2017/0296324 A1 10/2017 Argentine

FOREIGN PATENT DOCUMENTS

EP 2837362 A1 2/2015

OTHER PUBLICATIONS

PCT/US2020/034037, The International Search Report and the Written Opinion of the International Searching Authority, dated Aug. 7, 2020, 14 pages.

(Continued)

*Primary Examiner* — William H Matthews
(74) *Attorney, Agent, or Firm* — Innovation Counsel LLP

(57) ABSTRACT

The techniques of this disclosure generally relate to a stent-graft system including a bifurcated stent-graft, a first bifurcating branch device, and a first branch extension. The bifurcated stent-graft includes a body, a first branch limb, and a second branch limb. The first bifurcating branch device includes a body segment coupled to the first branch limb of the bifurcated stent-graft, a first branch limb, and a second branch limb. The first branch extension is within the first branch limb of the first bifurcating branch device and within an external iliac artery. The first bifurcating branch device has a wide patient applicability since the treatment can be extended proximal to the anatomical iliac bifurcation and is not limited by the common iliac artery length. The stent-graft system is suitable to treat a wide range of internal and external iliac artery diameters.

19 Claims, 11 Drawing Sheets

(51) Int. Cl.
    *A61F 2/856*    (2013.01)
    *A61F 2/06*     (2013.01)

(56) References Cited

OTHER PUBLICATIONS

S. Anton et al., "Initial Experience with the E-liac Iliac Branch Device for the Endovascular Aortic Repair of Aorto-iliac Aneurysm", Cardiovasc Intervent Radiol (2018), Jan. 3, 2018, pp. 683-691, Springer Science+Business Media, LLC, https://doi.org/10.1007/S00270-017-1868-x.

Gustavo S. Oderich et al., "Techniques of Endovascular Aortoiliac Repair Using an Iliac Branch Endoprosthesis", Preserving the Hypogastric Artery, Supplement to Endovascular Today, Aug. 2017, pp. 17-21, vol. 16, No. 8, Gore & Associates.

Gustavo S. Oderich et al., "Endovascular Iliac Branch Devices for Iliac Aneurysms", Perspectives in Vascular Surgery and Endovascular Therapy, 2011, pp. 166-172, 23(3), Sage Publications Inc., http://pvs.sagepub.com.

Darren B. Schneider et al., "Outcomes of the GORE Iliac Branch Endoprothesis in clinical trial and real-world registry settings", Journal of Vascular Surgery, Feb. 2019, pp. 367-378, https://doi.org/10.1016/j.jvs.2018.05.200.

C. Ferrer et al., "A Steerable Sheath to Deploy Hypogastric Bridging Stent by Contralateral Femoral Approach in an Iliac Branch Procedure after Endovascular Aneurysm Repair", Annals of Vascular Surgery, Elsevier, vol. 44, Oct. 2017, 415.e3, CrossMark.

"Heli-FX EndoAnchor System", Healthcare Professionals, EVAR and TEVAR Procedures, Dec. 2019, 2020 Medtronic, UC201801389b EN.

"TourGuide Steerable Sheath", Healthcare Professionals, EVAR and TEVAR Procedures, Feb. 2018, 2020 Medtronic, UC201801390EN.

\* cited by examiner

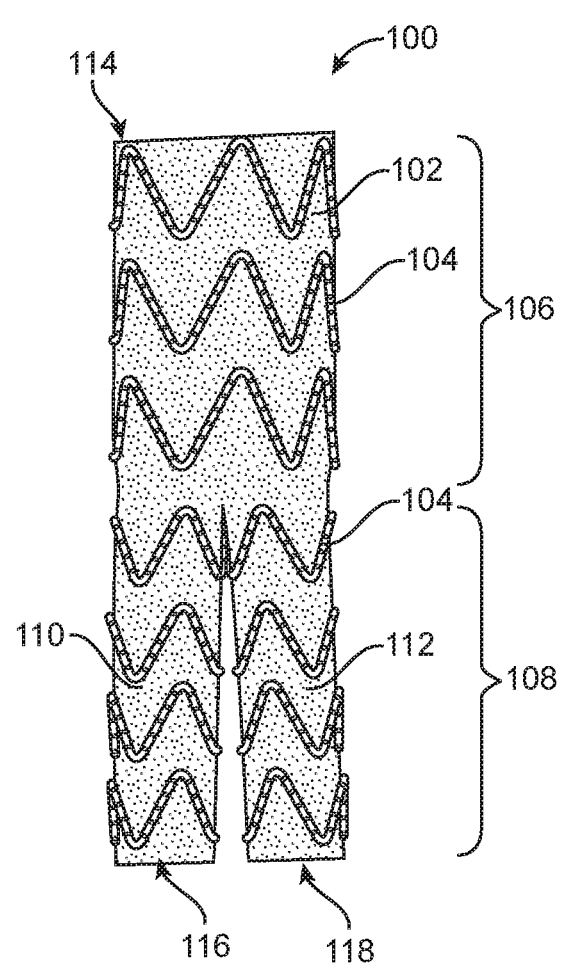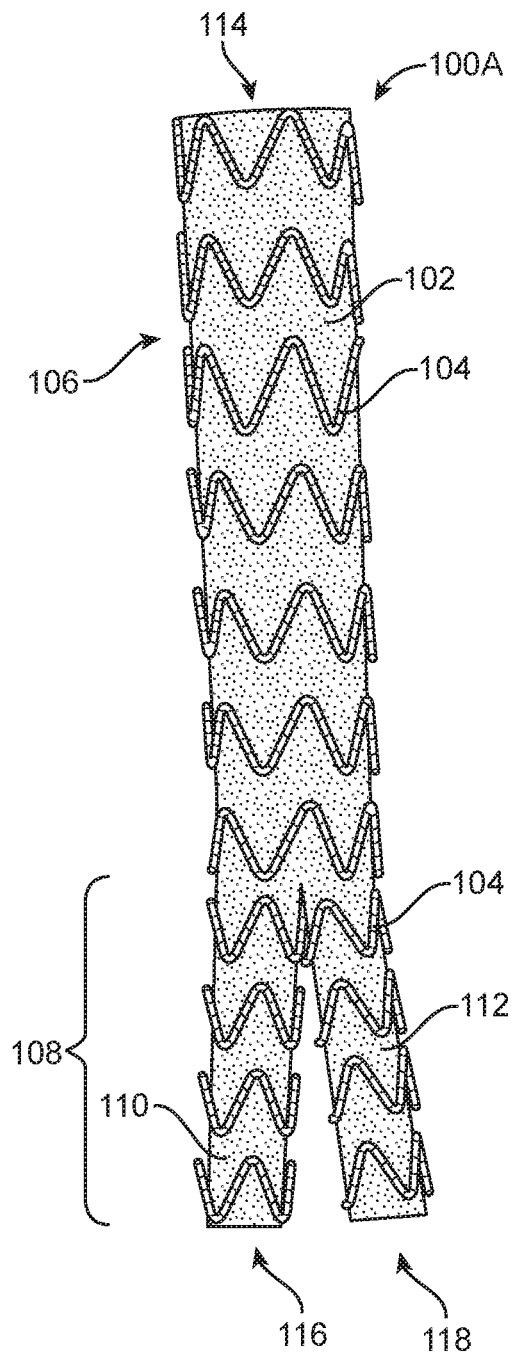
FIG. 1
FIG. 2

BIFURCATING BRANCH MODULAR ILIAC BRANCH DEVICE

CROSS-REFERENCE TO RELATED APPLICATIONS

This application claims the benefit of U.S. Provisional Application No. 62/855,163 filed on May 31, 2019, entitled "BIFURCATING BRANCH MODULAR ILIAC BRANCH DEVICE" of Keith Perkins et al., which is incorporated herein by reference in its entirety.

FIELD

The present technology is generally related to endovascular devices, for example, devices for treatment of a diseased aorta.

BACKGROUND

A conventional stent-graft typically includes a radially expandable reinforcement structure, e.g., formed from a plurality of annular stent rings, and a cylindrically shaped layer of graft material defining a lumen to which the stent rings are coupled. Endovascular aneurysmal exclusion is a method of using a stent-graft to exclude pressurized fluid flow from the interior of an aneurysm, thereby reducing the risk of rupture of the aneurysm and the associated invasive surgical intervention. Challenges may occur in patients with certain types of aneurysms, such as an iliac aneurysm. Often the short length of the common iliac artery may prevent patients from receiving endovascular aneurysmal exclusion therapy to treat the iliac aneurysm.

SUMMARY

The techniques of this disclosure generally relate to a stent-graft system including a bifurcated stent-graft, a first bifurcating branch device, and a first branch extension. The bifurcated stent-graft includes a body, a first branch limb, and a second branch limb. The first bifurcating branch device includes a body segment coupled to the first branch limb of the bifurcated stent-graft, a first branch limb, and a second branch limb. The first branch extension is within the first branch limb of the first bifurcating branch device and within an external iliac artery. The first bifurcating branch device has a wide patient applicability since the treatment can be extended proximal to the anatomical iliac bifurcation and is not limited by the common iliac artery length. The stent-graft system is suitable to treat a wide range of internal and external iliac artery diameters.

In one aspect, the present disclosure provides a method including deploying a bifurcated stent-graft within an aorta proximal to an aortic bifurcation, deploying a body segment of a first bifurcating branch device coupled to a first branch limb of the bifurcated stent-graft, and deploying a first branch extension within a first branch limb of the first bifurcating branch device and within a first vessel, e.g., the external iliac artery.

In another aspect, the present disclosure provides a bifurcating branch device including an upper segment and a lower segment. The upper segment includes a nonflared portion and a flared portion having a greater diameter than the nonflared portion. The lower segment includes a first branch limb and a second branch limb. The flared portion is located between the nonflared portion and the lower segment.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIG. 1 is a front view of a bifurcating branch device, according to one embodiment.

FIG. 2 is a front view of a bifurcating branch device having an extended limb portion, according to one embodiment.

DETAILED DESCRIPTION

Figure 3A:
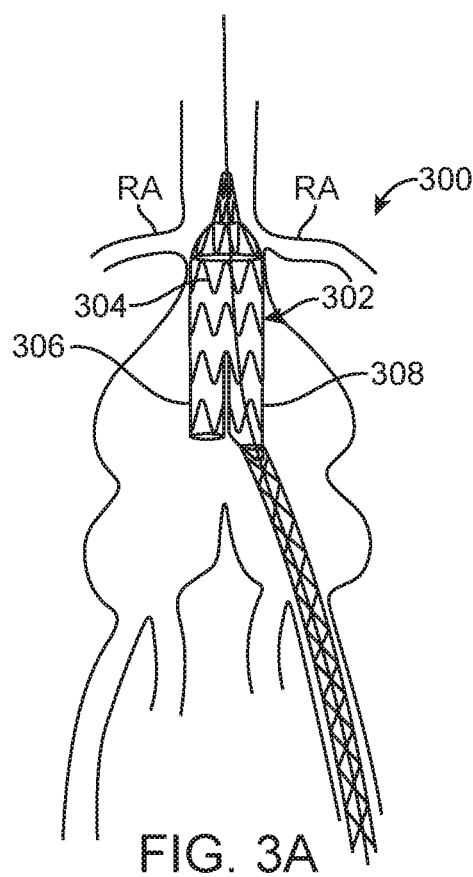
FIGS. 3A, 3B, 3C, 3D, 3E, 3F, 3G, 3H, 3I, 3J, 3K are schematic examples of a branching limb deployment sequence, according to one embodiment.

FIGS. 1 through 12G disclose examples of bifurcating branch devices, as well as stent-graft systems including the device(s) and example methods for deploying the devices and systems. The devices, systems, and methods may be used in the treatment of intra-vascular diseases, such as aneurisms. The devices, systems, and methods are described herein with respect to treating disease of the iliac arteries, however, one of ordinary skill in the art will understand that the devices, systems, and methods may be used in other areas of the vasculature and/or for other pathologies like aorto-iliac occlusive disease.

FIGS. 1 and 2 show examples of bifurcating branch device 100, 100A, respectively. The bifurcating branch devices 100, 100A may generally include a graft material 102 and one or more stents 104 attached to the graft material 102. In the embodiments shown, the stents 104 may include a plurality of spaced apart individual stent rings which are generally sinusoidal. Alternatively, there may be a single, continuous stent (e.g., a helical stent) or a combination of stent rings and continuous stents. The stents 104 may be self-expanding structures, e.g., formed of nickel titanium alloy (nitinol), or other shaped memory material, or they may be balloon expandable stents. The graft material 102 may be any suitable graft material known to be utilized in vascular grafts. For example, the graft material 102 may be a non-permeable material, e.g., a polyester terephthalate (PET), expanded polyester terephthalate (ePET), or polytetrafluoroethylene (PTFE) based material, or other non-permeable graft material.

As shown in FIGS. 1 and 2, the bifurcating branch devices (BBDs) 100/100A may include an upper segment 106 and a lower segment 108. The upper segment 106 may be referred to as the body or the limb segment 106. As described in greater detail below, the upper segment 106 may be configured to be deployed within a previously deployed stent-graft, for example, in a more proximal region of the aorta, e.g., an abdominal aortic aneurism (AAA) device. The lower segment 108 may be a bifurcated segment including two articulating limbs 110, 112, which may be referred to as branch limbs 110, 112. The limbs 110, 112 may articulate or move independent of each other along substantially their entire length, e.g., except at the point of bifurcation.

In at least one embodiment, the bifurcated limbs 110, 112 may extend in a direction parallel to the upper segment 106, e.g., their longitudinal axes may be parallel. The relative directions of the limbs 110, 112 and the upper segment 106 may refer to the bifurcating branch devices 100/100A being in an unconstrained position, for example, as it exists outside of the body or a delivery system, e.g., as shown in FIG. 1. The legs may not be perfectly parallel to the upper body, such as shown in FIG. 2, but may generally extend in the same direction, e.g., within 5 or 10 degrees of parallel. This description of the relative directions of bifurcated limbs 110, 112 relative to their upper non-bifurcated portions 106 may apply to any bifurcated device described herein.

The body segment 106 may define a body lumen 114 that is configured to receive blood flow from proximal to the bifurcating branch devices 100/100A. The blood may then flow into branch lumens 116, 118 defined by the branch limbs 110, 112, respectively. In one embodiment, all blood that enters the body lumen 114 exits the bifurcating branch devices 100/100A through the branch lumens 116, 118.

The bifurcating branch devices 100/100A in FIGS. 1 and 2 are shown with some example dimensions, however, it is to be understood that these dimensions are strictly examples and are not intended to be limiting. In one example, the diameter of the body segment 106 may be approximately 16 mm, such as 10 to 25 mm, or any sub-range therein, e.g., 12 to 20 mm, 12 to 18 mm, or 14 to 18 mm. In the example shown in FIG. 1, the body segment 106 may have a length of approximately 30 mm, such as 20 to 40 mm, or any sub-range therein, e.g., 25 to 35 mm.

In both FIGS. 1 and 2, the two branch limbs 110, 112 of each bifurcating branch devices 100/100A are shown as having the same diameter. In one embodiment, both branch limbs 110, 112 may be approximately 8 mm, such as 6 to 14 mm, or any sub-range therein, e.g., 6 to 12 mm, 6 to 10 mm, 8 to 12 mm. In the example shown in FIG. 2, the body segment 106 may be substantially longer than the body segment 106 of FIG. 1. For example, the body segment 106 in FIG. 2 may have a length of at least 50 mm or 60 mm, such as 50 to 100 mm, or any sub-range therein.

With reference to FIGS. 3A-3K, an example deployment sequence of a stent-graft system 300 is shown. Each of FIGS. 3A-3K in the sequence is referred to herein as a step, however, it is to be understood that some portions of the deployment may occur between each shown step.

In a first step as shown in FIG. 3A, an initial stent-graft 302 may be deployed in the aorta proximal to the aortic bifurcation. In the example shown, the stent-graft 302 is deployed with its proximal end near the renal arteries RA. In one embodiment, the stent-graft 302 may be a AAA device 302 that includes a bifurcation, such as one of the Endurant devices from Medtronic, Inc. Similar to the BBD 100, the bifurcated stent-graft 302 may include a body 304 and two branch limbs 306, 308.

In FIG. 3A, the stent-graft 302 is partially deployed, with one branch limb 306 fully deployed and the other branch limb 308 only partially deployed. In the embodiment shown, the branch limbs 306, 308 have different lengths, however, in other embodiments the limb lengths may be the same.

Figure 3B:
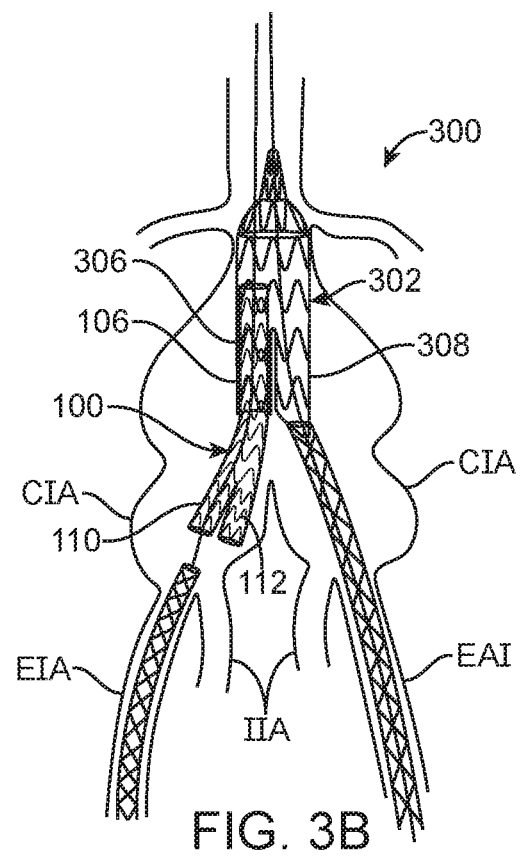

In step two as shown in FIG. 3B, with one branch limb 308 still partially deployed, BBD 100, i.e., body segment 106, is deployed within the already deployed branch limb 306 of the AAA device 302. In the following sequence, BBD 100 of FIG. 1 is illustrated and discussed, however, the discussion is equally applicable to BBD 100A of FIG. 2 or any of the BBDs as disclosed herein. When the BBD 100 is deployed, the branch limbs 110, 112 may extend into the common iliac artery CIA, which may be aneurysmal.

Figure 3C:
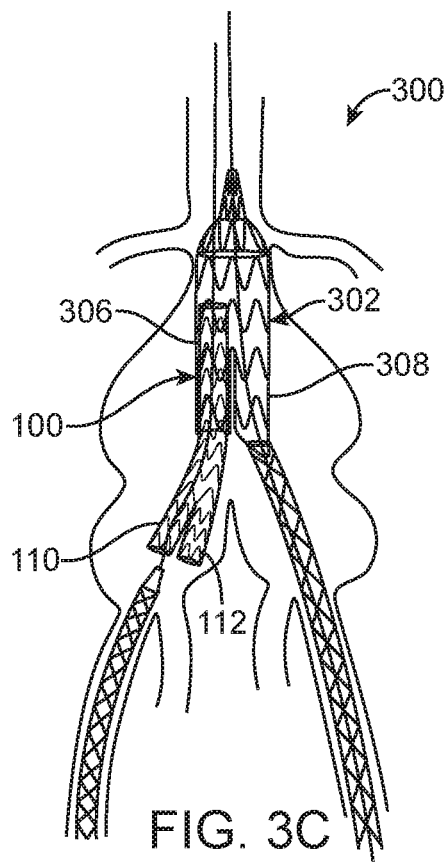
Figure 3D:
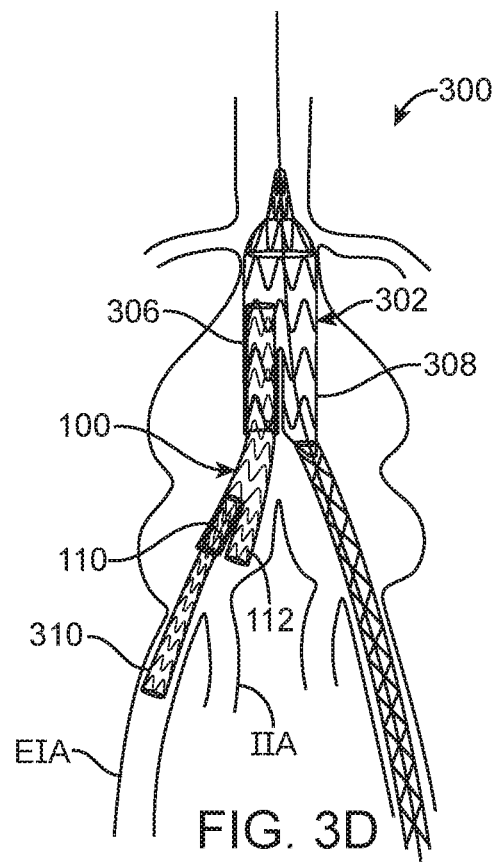

In steps three and four as shown in FIGS. 3C and 3D, a branch extension 310 may be delivered to the BBD 100 and deployed within one branch limb 110 of the BBD 100. The branch extension 310 may extend from the branch limb 110 to a non-aneurysmal portion of the external iliac artery EIA.

In the embodiment shown, the first branch extension 310 may extend into the external iliac artery EIA, however, in another embodiment it may be in the internal iliac artery IIA. The branch extension 310 may be comprised of generally similar components to the BBD 100, e.g., a graft material and one or more stents. However, the specific materials of the graft and stents may differ from that of the BBD 100, depending on the application, patient anatomy, or other considerations.

Figure 3E:
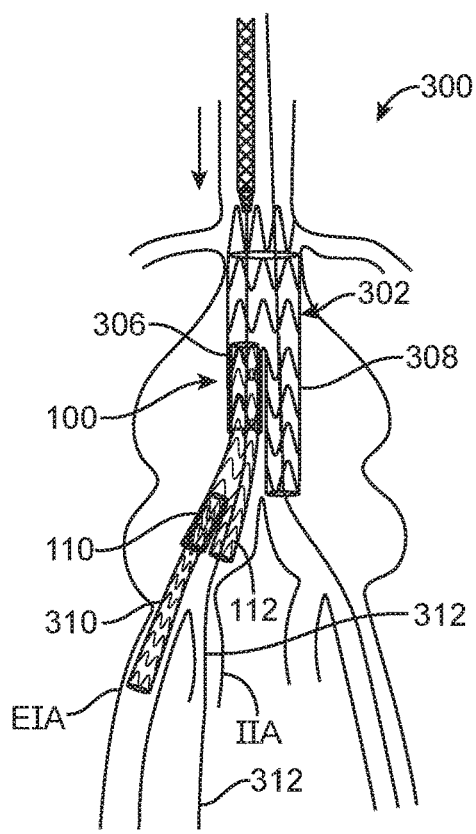
Figure 3F:
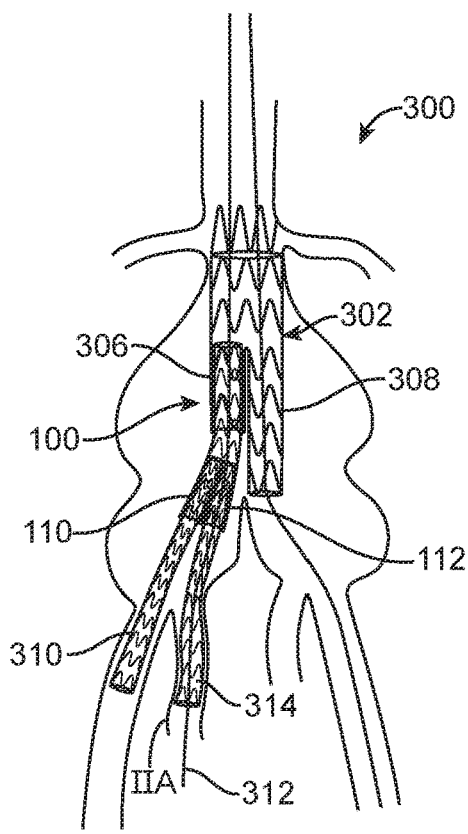

In step five as shown in FIG. 3E, the other branch limb 308 of the AAA device 302 may be fully deployed. In addition, a guidewire 312 may be introduced through the second branch limb 112 of the BBD 100 via supra-aortic access. In steps five and six as shown in FIGS. 3E and 3F, a second branch extension 314 may be delivered to the BBD 100 and deployed within the second branch limb 112 of the BBD 100. The second branch extension 314 may extend into whichever iliac artery was not occupied by the first branch extension 310. In the embodiment shown, the second branch extension 314 extends into the internal iliac artery IIA.

If only one of the common ilia arteries CIA is aneurysmal, the deployment may cease after step six as shown in FIG. 3F, with the exception of a possible extension from the second branch limb 308 of the AAA device 302 to the other contralateral common iliac artery CIA.

Figure 3G:
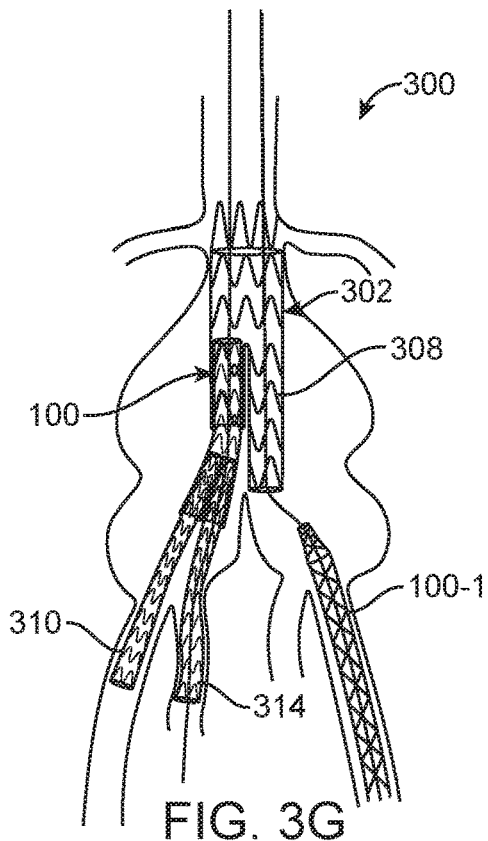
Figure 3H:
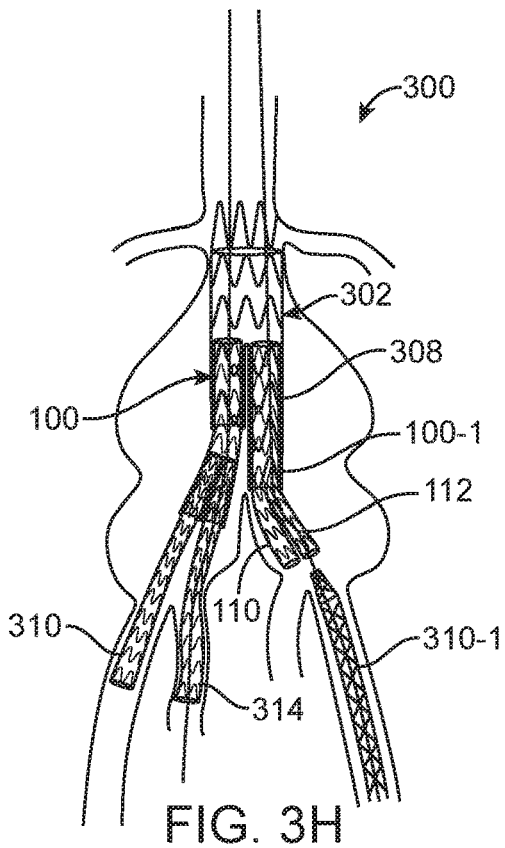
Figure 3I:
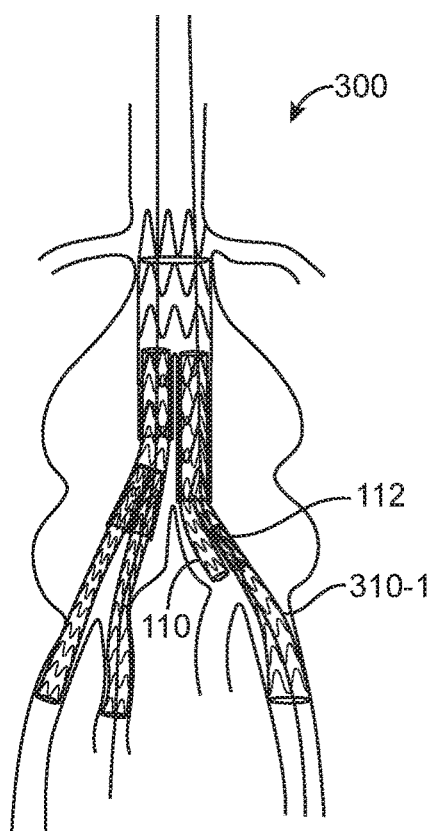
Figure 3J:
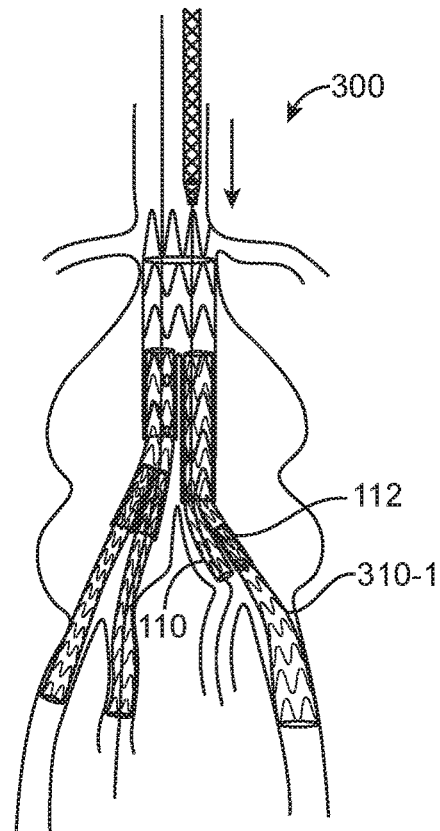
Figure 3K:
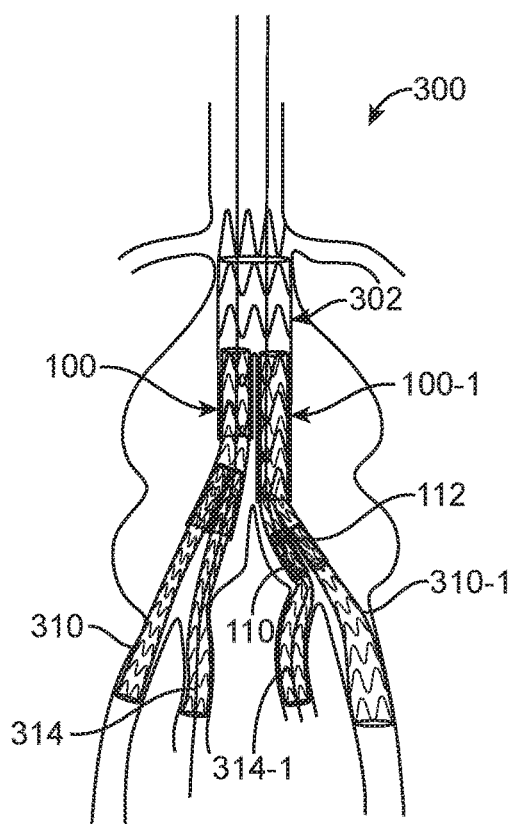

However, if both common ilia arteries CIA are aneurysmal, then a second BBD 100-1 may be deployed in a manner similar to steps one to six as shown in FIGS. 3A-3F. In step seven as shown in FIG. 3G, the second BBD 100-1 may be delivered to the second branch limb 308 of the AAA device 302. In steps eight and nine as shown in FIGS. 3H and 3I, a branch extension 310-1, sometimes called a third branch extension 310-1, may be deployed within one branch limb 110 or 112 (branch limb 112 in the embodiment shown) of the BBD 100-1 and the branch extension 310-1 may extend into the external iliac artery EIA. In steps ten and eleven as shown in FIGS. 3J and 3K, a second branch extension 314-1 may be delivered to the second branch limb 110 of the BBD 100-1, for example via supra-aortic access. The second branch extension 314-1 may extend from the second branch limb 110 into the other iliac artery, the internal iliac artery IIA in the example shown. Following step eleven as shown in FIG. 3K, all guidewires and catheters may be removed and a complete stent-graft system 300 may be in place to cover blood flow from the abdominal aorta through either one or both sets of iliac arteries. Note branch extensions 310-1, 314-1 are sometimes called third and fourth branch extensions 310-1, 314-1.

Figure 4:
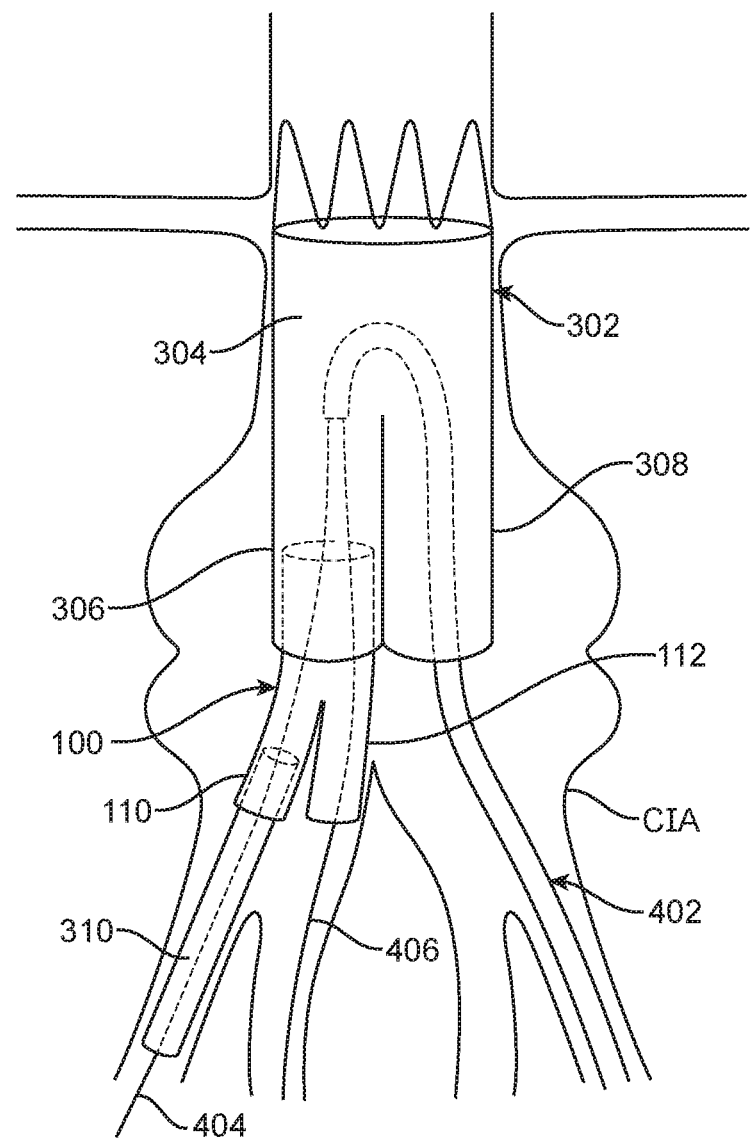
FIGS. 4 and 5 are schematic examples demonstrating deployment methods in accordance with various embodiments.
Figure 5:
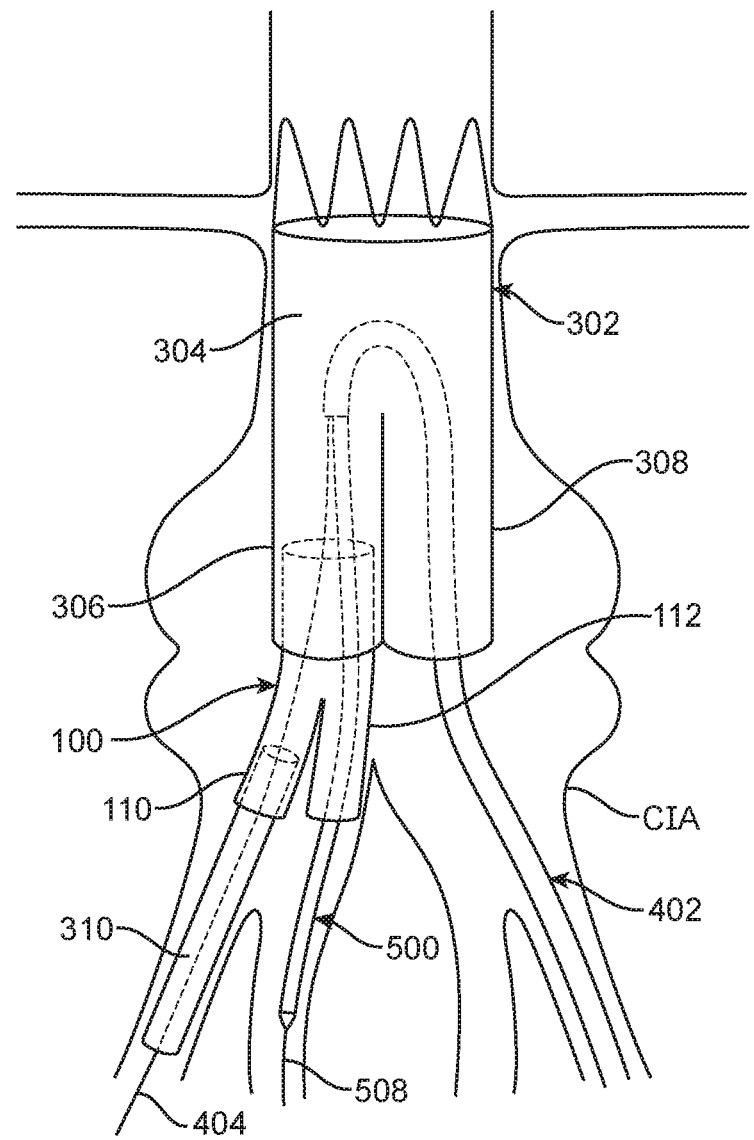

With reference to FIGS. 4 and 5, an example is shown of an alternative deployment method that avoids the use of supra-aortic access, if such access is not possible or desired. In this example, access is achieved from the contralateral side instead of through supra-aortic access.

FIG. 4 is an alternative to the deployment step 5 shown in FIG. 3E. From FIG. 3D, deployment proceeds to FIG. 4 in accordance with this embodiment. Paying particular now attention to FIG. 4, the other branch limb 308 of the AAA device 302 may be fully deployed. A steerable catheter 402, sometimes called a steerable/deflectable sheath or guide, is advanced through the contralateral side, e.g., through the contralateral common iliac artery CIA and into the distal end of branch limb 308 of AAA device 302.

Upon reaching the bifurcation of body 304 and the branch limbs 306, 308, the obturator (if present) may be removed and the distal tip of the steerable catheter 402 may be deflected into a curved configuration (may be called a shepherds crook configuration), to point over the bifurcation (also called the flow divider) in the AAA device 302 and distally into the branch limb 306 of the AAA device 302. In particular, the distal tip of the steerable catheter 402 may be aimed or directed at the branch limb 112 of the BBD 100. In the embodiment shown in FIGS. 4 and 5, the distal tip of the steerable catheter 402 is disposed between the proximal end of the AAA device 302 and its bifurcation/flow divider. However, in other embodiments, the distal tip may be disposed anywhere above the bifurcation/flow divider, for example, the distal tip may be located above the AAA device 302 but may be aimed/directed downward into the branch limb 306 of the AAA device 302, such as directed at the branch limb 112 of the BBD 100.

The steerable catheter 402 may be any catheter configured to bend or deflect its distal end more than 90 degrees such that it faces at least partially back towards its proximal end. In one embodiment, the distal tip may be deflected with a radius of curvature of less than or equal to 25 mm, such as less than or equal to 20 mm, 18 mm, or less. In one example the radius of curvature may be about 17 mm and generally between 16-26 mm. The steerable catheter 402 may include one or more wires attached at or near the distal tip, which may be manipulated to generate the deflection of the tip.

In one embodiment, referring now to FIGS. 4 and 5 together, the steerable catheter 402 is engineered to specifically provide the support needed to deliver a branch extension delivery system 500, as illustrated in FIG. 5. More particularly, a guidewire 508 is advanced through the steerable catheter 402 and into the internal iliac artery IIA.

With reference to FIG. 5, the branch extension delivery system 500 for delivering the second branch extension 314 is advanced through the steerable catheter 402 and over the guidewire 508 to be located within the branch limb 112 and the internal iliac artery IIA. The steerable catheter 402 is robust enough to maintain the imparted curvature while tracking the relatively stiff branch extension delivery system 500 therethrough. The second branch extension 314 is deployed to bridge the branch limb 112 and the internal iliac artery IIA as shown at step 6 in FIG. 3F.

In another embodiment, referring again to FIG. 4, using a buddy catheter inside of the steerable catheter 402, a guidewire 404, sometimes called a sheath reinforcing through-and-through (TnT) wire, is run up and over the AAA bifurcation into a nested sheath on the contralateral side. The guidewire 404 is externalized by tracking into the external iliac artery EIA and externalized through a femoral access site as illustrated in FIG. 4. The guidewire 404 extends from the steerable catheter 402 into the external iliac artery EIA and is externalized. In one embodiment, the guidewire 404 is snared to externalize the guidewire 404 though the external iliac artery EIA.

Further, a soft guidewire 406 is introduced inside of the buddy guide catheter through the hemostatic valve of the steerable catheter 402 and advanced to the internal iliac artery IIA. Once the internal iliac artery IIA is cannulated, a wire exchange is performed to exchange the soft guidewire 406 for a moderately stiff guidewire 508 (illustrated in FIG. 5).

With reference to FIG. 5, the branch extension delivery system 500 for delivering the second branch extension 314 is advanced through the steerable catheter 402 and over the stiff guidewire 508 to be located within the branch limb 112 and the internal iliac artery IIA. While the branch extension delivery system 500 is being delivered, constant tension is maintained on the guidewire 404 to keep the steerable catheter 402 from straightening out. The second branch extension 314 is deployed to bridge the branch limb 112 and the internal iliac artery IIA as shown at step 6 in FIG. 3F. The branch extension delivery system 500, the steerable catheter 402, and the guidewires 404, 508 are then removed.

Although the guidewire 404 is illustrated in FIGS. 4-5 and discussed, in the embodiment where the steerable catheter 402 is robust enough to maintain the imparted curvature while tracking the relatively stiff branch extension delivery system 500 therethrough, the guidewire 404 is not used and thus would not appear in the figures. Suitably, if use of the guidewire 404 is avoided, the procedure is simplified.

A suitable example of the branch extension delivery system 500 is the iCAST delivery system from Atrium.

The branch extensions, e.g., 310, 314, in any of the embodiments described herein may be formed of any suitable material, such as a PET based material or a PTFE based material. In one example, the branch extensions 310, 314 may be a covered stent wherein the stent is disposed/laminated between sheets of graft material, such as PTFE. One example of such a suitable branch extension is the iCAST balloon-expandable covered stent from Atrium. It has been found that for smaller diameter grafts, a PTFE based material may result in less occlusion of the stent-graft over time. Accordingly, a PTFE based material may be used in the branch extensions, particularly those having smaller diameters (e.g., less than 10 mm).

In one embodiment, the second branch extension 314-1 as shown in FIG. 3K is also deployed from the contralateral side using a method similar to the contralateral access method of FIGS. 4 and 5 as those of skill in the art will understand in light of this disclosure.

Figures 6A, 6B:
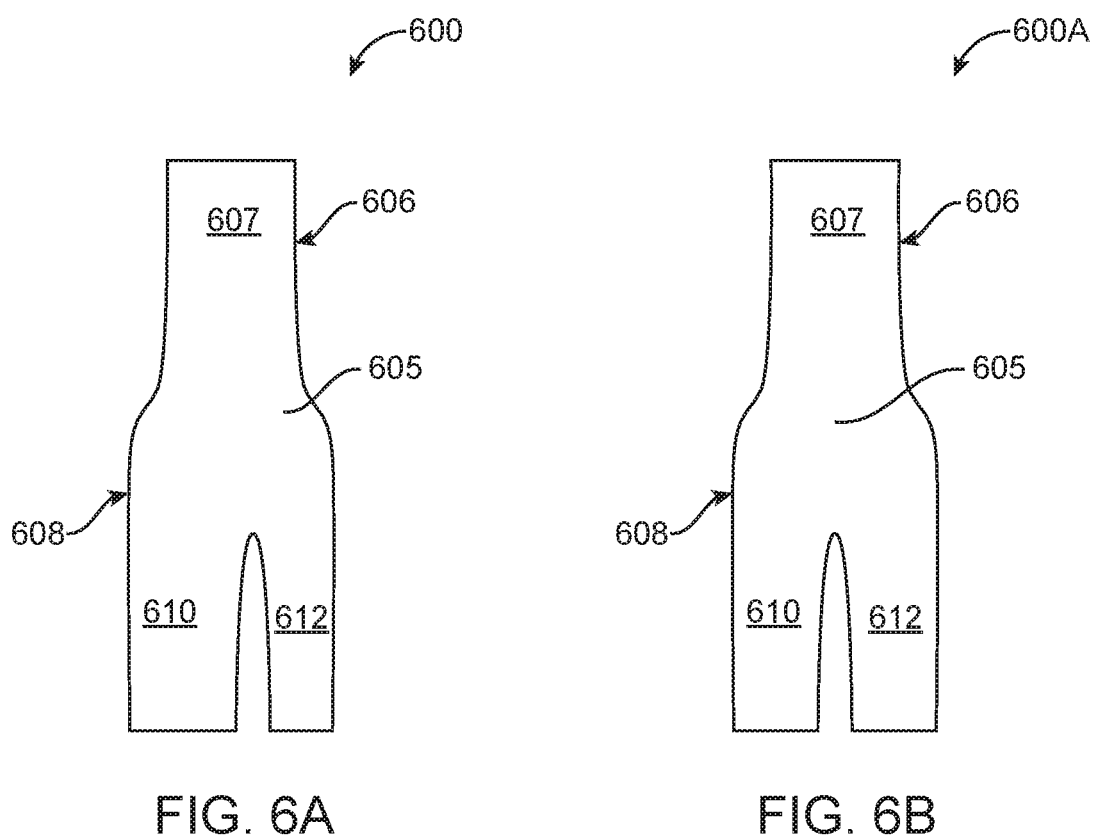
FIGS. 6A and 6B are front schematic views of two example bifurcating branch devices in accordance with various embodiments.

With reference to FIGS. 6A and 6B, examples are shown of bifurcating branch devices 600 and 600A that are similar to those described above, but with a flare 605, sometimes called the flared portion 605. More particularly, a body segment 606 includes a nonflared proximal portion 607 and the flared portion 605. The flared portion 605 is a flare, or increase, in the diameter between the proximal portion 607 of the body segment 606 and a bifurcated or lower segment 608. The flare 605 may cause an increase in the diameter of the BBD 600/600A such that a total diameter of the branch limbs 610, 612 may be greater than the diameter of the proximal portion 607 of the body segment 606.

The diameter of the proximal portion 607 of the body segment 606 and the length of the bifurcated segment 608 may be similar to those described above with reference to FIGS. 1 and 2. In one embodiment, the flared portion 605 may have a diameter of approximately 20 mm, such as 18 to 26 mm, or any sub-range therein, e.g., 18 to 24 mm, 18 to 22 mm, or 20 to 24 mm. In the embodiments shown in FIGS. 6A and 6B, the total length of the BBD 600/600A may be longer than the embodiment shown in FIG. 1 but shorter than the embodiment shown in FIG. 2. In one example, the BBD 600/600A may have a total length of approximately 70 mm or 80 mm, such as 60 to 90 mm, or any sub-range therein, e.g., 60 to 80 mm, 65 to 85 mm, 65 to 80 mm, or 65 to 75 mm.

In the examples shown, the proximal portion 607 of the body segment 606, e.g., the non-flared portion, may have a length of approximately 30 mm or 40 mm, such as 20 to 50 mm, or any sub-range therein, e.g., 25 to 50 mm, 25 to 45 mm, 30 to 50 mm, 30 to 45 mm, or 30 to 40 mm. The length of the non-flared portion 607 may depend on the number of stent rings to be included in said portion. For example, if there are three stent rings, the length may be approximately 30 mm, but if a fourth stent ring is added, then the length may be approximately 40 mm. The flared portion 605 of the BBD 600/600A may have a diameter that is at least 2 mm larger than the proximal diameter, such as 2 to 10 mm larger, or any sub-range therein, e.g., 2 to 8 mm, 2 to 6 mm, or 2 to 4 mm. In one embodiment, the flared portion 605 may have a length of approximately 10 mm, such as 5 to 20 mm, or any sub-range therein, e.g., 5 to 15 mm, 6 to 14 mm, 8 to 14 mm, 8 to 12 mm, or 10 to 12 mm.

In one non-limiting example, the diameter of the BBD 600/600A may flare from approximately 16 mm at the proximal portion 607 of the body segment 606 to approximately 20 mm at the transition (flare 605) from the body segment 606 to the bifurcated segment 608. This may allow for branch limbs 610, 612 having diameters that add up to greater than the approximately 16 mm body diameter—approximately 10 mm and 8 mm in FIG. 6A and approximately 10 mm and 10 mm in FIG. 6B.

The BBDs 600/600A of FIGS. 6A and 6B having flared portions 605 may allow for the treatment of external iliac arteries EIAs or internal iliac arteries IIAs having larger diameters than that of FIGS. 1 and 2, e.g., about 8 mm. One or both of the branch limbs 610, 612 may have a larger diameter, such as approximately 10 mm or larger, e.g., 9 to 14 mm, 9 to 12 mm, or 10 to 12 mm. In one non-limiting example of FIG. 6A, the left branch limb 610 is larger and is configured for an external iliac artery EIA of 10 mm or larger. The right branch limb 612 is smaller, approx. 8 mm, and is configured for an internal iliac artery IIA of less than 10 mm. In one non-limiting example of FIG. 6B, both branch limbs 610, 612 are larger and are configured for an external iliac artery EIA and an internal iliac artery IIA of 10 mm or larger.

The devices, stent-graft systems, and methods described herein may address one or more therapy gaps in the commercially available endovascular treatment space. For example, up to an estimated 30% of AAAs involve the iliac arteries. Common iliac artery (CIA) diameters of >20 mm have been shown to be independent predictors of late sac enlargement. Inadequate iliac fixation may cause stent graft migration and aneurysm sac pressurization leading to increased rupture risk and driving the need for costly and invasive secondary interventions. Current treatment options for iliac disease include intentional coverage of a single internal iliac artery. This can result in neurological injury, buttock claudication, impotency, spinal cord ischemia, and bowel infarcts. A few commercial off the shelf iliac branch stent grafts are available to allow for continued perfusion of the internal iliac artery, but they are severely limited in terms of patient anatomies they can treat. Estimates are that only 35% of repairs can be done "on label" with the current devices approved for sale in the US.

The BBDs disclosed herein have wide patient applicability since the treatment can be extended proximal to the anatomical iliac bifurcation and is not limited by the common iliac artery length. The device design is suitable to treat a wide range of internal and external iliac artery diameters. Supra-aortic access allows for direct cannulation access of internal and external iliac arteries without the procedural complexities required of crossover techniques. Easily adaptable to bilateral hypogastric perfusion. Articulating nature of the limb gates eases cannulation and allows for more natural and sweeping branch stent configurations.

One advantage of the BBD may be the flow divider in the bifurcation segment, which mimics natural anatomy. There is a transition from Aortic body to limb segments, and the smooth transition prevents flow disturbances that could lead to thrombosis of the device and attached limb stents. The design allows limb segments to achieve high angulation, up to 180 degrees and/or prolapse, without kinking or compromise of intralumenal flow areas. The unique transition at the flow divider promotes flexibility and enables the limb segments to achieve high angulation without kinking or compromise of intralumenal flow area.

Other advantages include: (1) additional patient applicability—can treat the diseased common iliac artery without seating below the aortic bifurcation; (2) flexible transition—designed to treat a variety of anatomical states; (3) additional flexibility of articulating limb segments facilitates cannulation; and (4) lining the limbs with a balloon expandable (BE) stent reduces graft material in-folding which further limits flow disturbances in the limbs that can lead to thrombosis.

Regarding the articulating limbs, advantages include: (1) length of the pre-cannulated limb segment can be varied to provide a mechanism to stabilize the device during cannulation and branching of the internal iliac artery; (2) the internal luminal surfaces of the limb segments can be coated with an anti-thrombogenic agent, such as heparin, etc. to further mitigate the risk of thrombotic occlusion; (3) design allows for the placement of BE stents in the articulating limb segments which is advantageous in target vessels that are 10*mm* or less; (4) for vessels larger than 10 mm, traditional self-expanding (SE) stents (e.g., PET covered) could be utilized; (5) associated diameters of the articulating limb segments can be up-sized to ensure compatibility for treatment in this situation (target vessels >10 mm); (6) geometry enables simple cannulation of the articulating limb segments from above, via supra-aortic access, or from below via a contralateral cross-over technique; (7) external branch is pre-cannulated by the delivery system and thus does not require separate cannulation to perfuse the target branch; and (8) saves time, radiation exposure, and use of contrast during clinical procedure.

Figure 7:
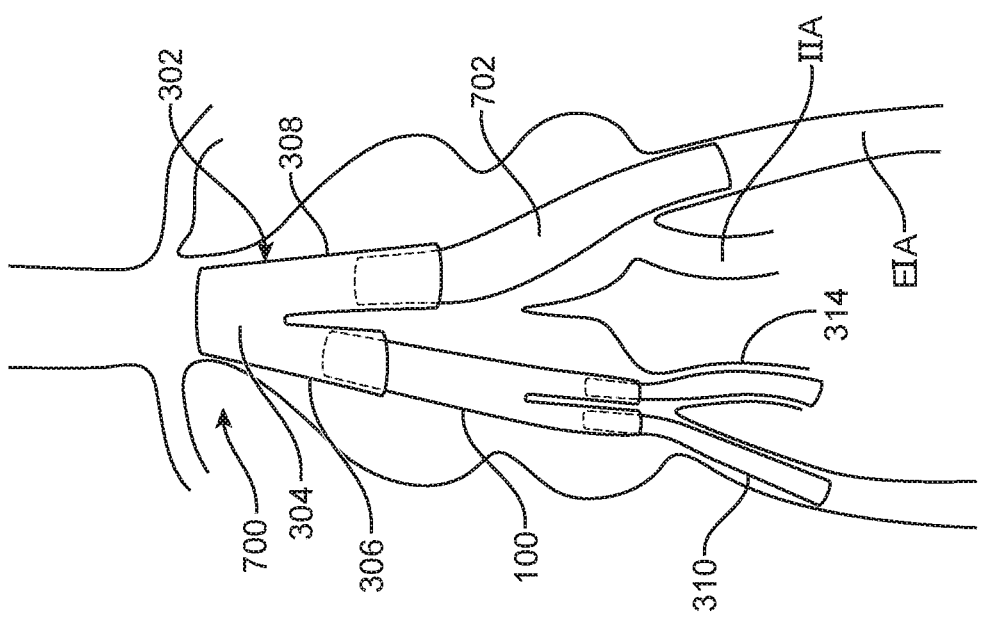
FIG. 7 is a schematic view of a stent-graft system in accordance with one embodiment.

FIG. 7 is a schematic view of a stent-graft system 700 in accordance with one embodiment. Stent-graft system 700 of FIG. 7 is similar to stent-graft system 300 as stage 11 as illustrated in FIG. 3K except includes a branch extension 702 instead of BBD 100-1 and branch extensions 310-1, 314-1. More particularly, branch extension 702 extends from the inside of branch limb 308 of stent-graft 302 to the external iliac artery EIA and the internal iliac artery IIA is bypassed. Illustratively, a total length of BBD 100 is 60, 93, 124, 156, or 199 mm depending upon the particular application of BBD 100.

Figure 8:
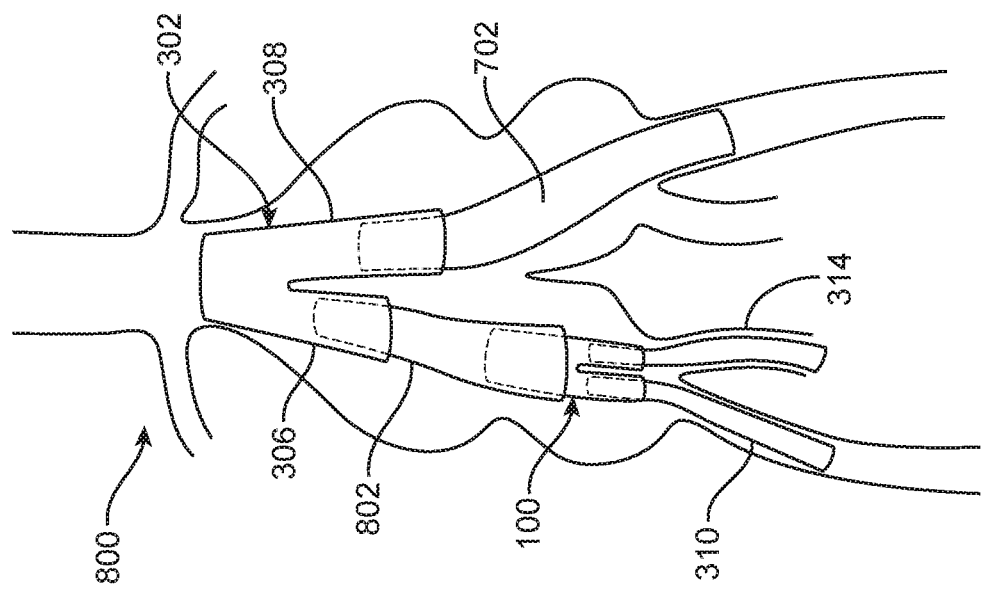
FIG. 8 is a schematic view of a stent-graft system in accordance with one embodiment.

FIG. 8 is a schematic view of a stent-graft system 800 in accordance with one embodiment. Stent-graft system 800 of FIG. 8 is similar to stent-graft system 700 of FIG. 7 except includes an additional branch extension 802 coupling BBD 100 and branch limb 306. More particularly, branch extension 802 is deployed within the branch limb 308 of stent-graft 302. BBD 100 is deployed within the branch extension 802.

Figure 9:
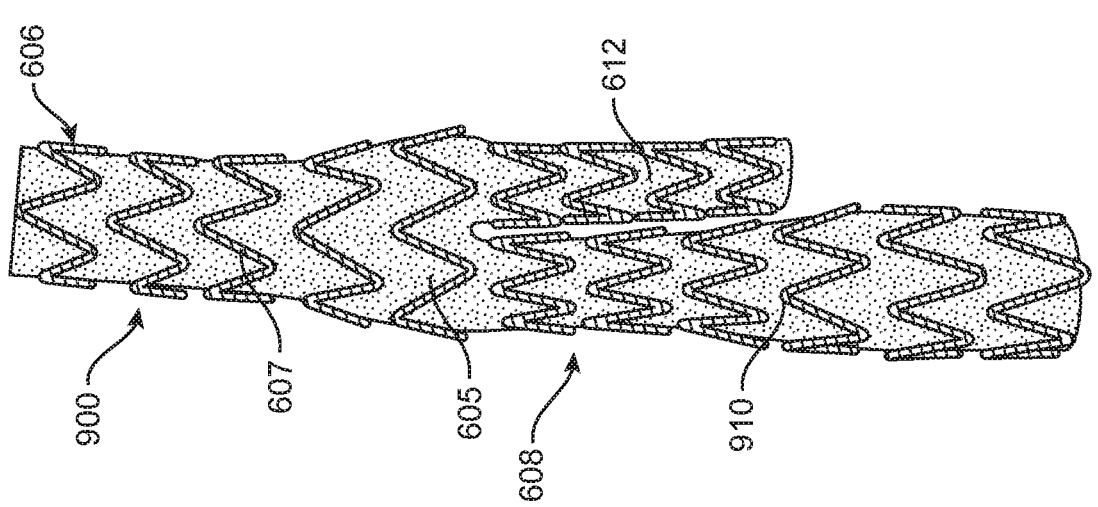
FIG. 9 is a schematic view of an asymmetric bifurcated branch device (ABBD) in accordance with another embodiment.

FIG. 9 is a schematic view of an asymmetric bifurcated branch device (ABBD) 900 in accordance with another embodiment. The ABBD 900 is similar to the BBD 600 of FIG. 6 except a length of a branch limb 910 is greater than a length of the branch limb 612 and so the ABBD 900 is asymmetrical. Illustratively, the diameter and the length of the proximal portion 606 are 16 mm and 30 mm, respectively, the length of the flared portion 605 is 20 mm, the diameter and the length of the branch limb 612 is 8 mm and 30 mm, respectively, and the length of the branch limb 910 is greater than 30 mm. As further examples, the diameter at the distal end of the branch limb 910 is 10, 13, or 16 mm. All dimensions are approximate, e.g., within +/−2 mm.

In the embodiment shown, the distal end of the branch limb 910 may be flared such that is has a larger diameter than near the bifurcation. In other embodiments, the branch limb 910 may have a constant (or substantially constant) diameter, such as in FIGS. 1 and 2. While the ABBD 900 is shown with a flared portion 605, it may also be configured without a flared portion, such as in FIGS. 1 and 2.

Figure 10:
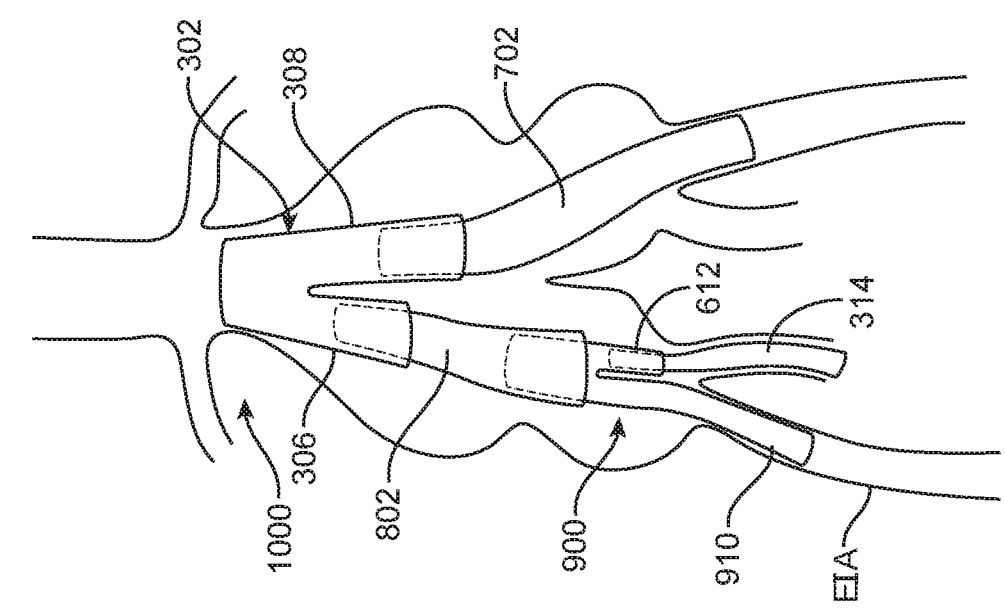
FIG. 10 is a schematic view of a stent-graft system including the ABBD of FIG. 9 in accordance with one embodiment.

FIG. 10 is a schematic view of a stent-graft system 1000 including the ABBD 900 of FIG. 9 in accordance with one embodiment. The stent-graft system 1000 of FIG. 10 is similar to the stent-graft system 800 of FIG. 8 and only the difference between the systems 1000, 800 are discussed below. The ABBD 900 is deployed within the branch extension 802 and the branch limb 910 extends directly into the external iliac artery EIA.

In one embodiment, the stent-graft 302 is initially deployed, the branch extension 802 is then deployed, and then the ABBD 900 is deployed. The branch limb 314 is then deployed through supra-aortic access or using the cross-over technique discussed above as desired.

Figure 11:
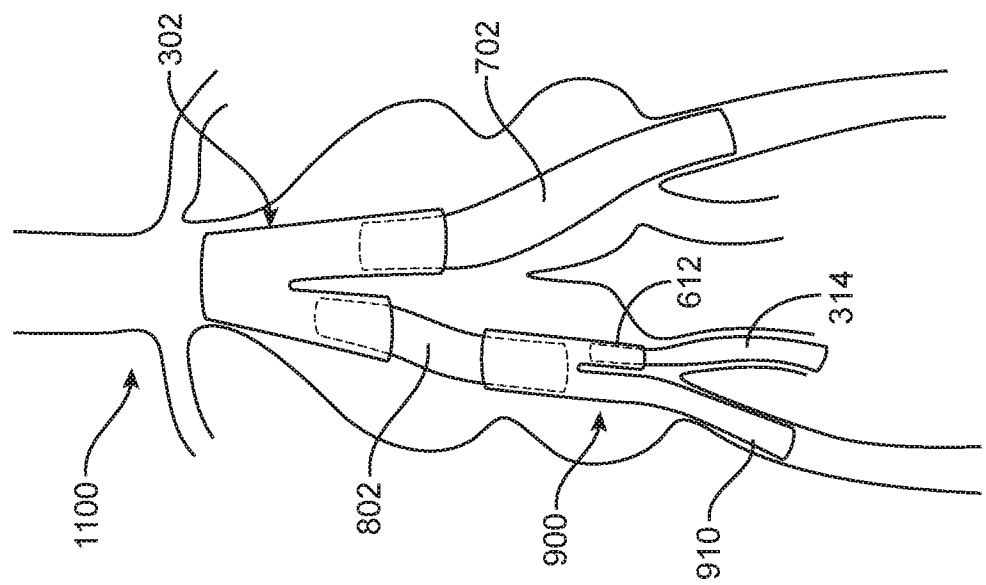
FIG. 11 is a schematic view of a stent-graft system including the ABBD of FIG. 9 in accordance with one embodiment.

FIG. 11 is a schematic view of a stent-graft system 1100 including the ABBD 900 of FIG. 9 in accordance with one embodiment. The stent-graft system 1100 of FIG. 11 is similar to the stent-graft system 1000 of FIG. 10 and only the difference between the systems 1100, 1000 are discussed below. As illustrated in FIG. 11, in accordance with this embodiment, the branch extension 802 is deployed within the stent-graft 302 and the ABBD 900.

For example, the ABBD 900 is initially deployed. The branch extension 314 is then deployed, e.g., through supra-aortic access or using the cross-over technique discussed above as desired. The stent-graft 302 is then deployed, at least partially. The branch extension 802 is deployed within the stent-graft 302 and the ABBD 900. Further, the branch extension 702 is deployed. In one embodiment, stent-graft system 1100 is deployed using a method similar to that discussed below in reference to FIGS. 12A-12G.

Figure 12A:
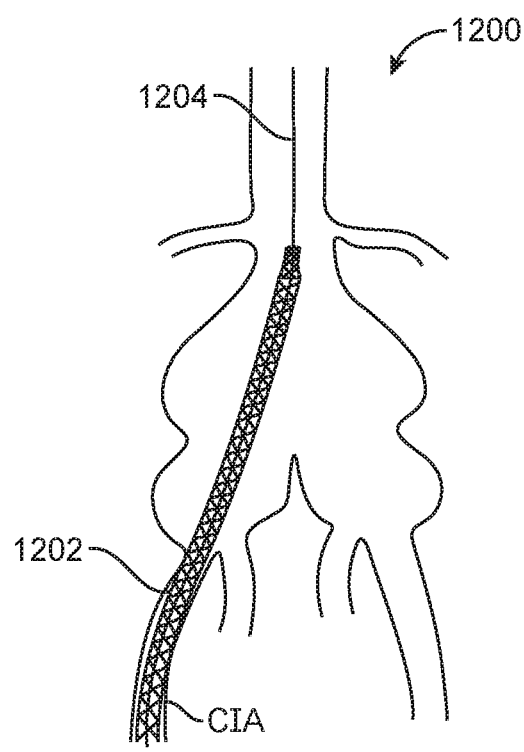
FIGS. 12A, 12B, 12C, 12D, 12E, 12F, 12G are an example deployment sequence of a stent-graft system in accordance with one embodiment.
Figure 12B:
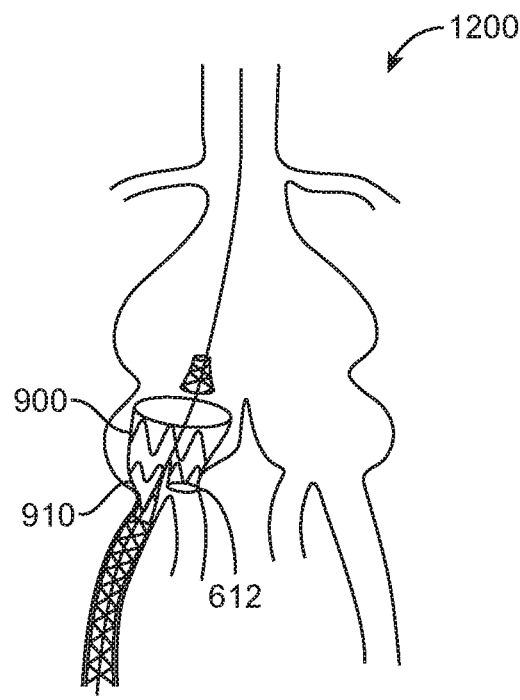

With reference to FIGS. 12A-12G, an example deployment sequence of a stent-graft system 1200 is shown. Each of FIGS. 12A-12G in the sequence is referred to herein as a step, however, it is to be understood that some portions of the deployment may occur between each shown step. In a first step as shown in FIG. 12A, a delivery system 1202 including the ABBD 900 is advanced over a guidewire 1204 into the common iliac artery CIA. In a second step as shown in FIG. 12B, the ABBD 900 is partially deployed, with the branch limb 612 fully deployed and the other branch limb 910 only partially deployed.

Figure 12C:
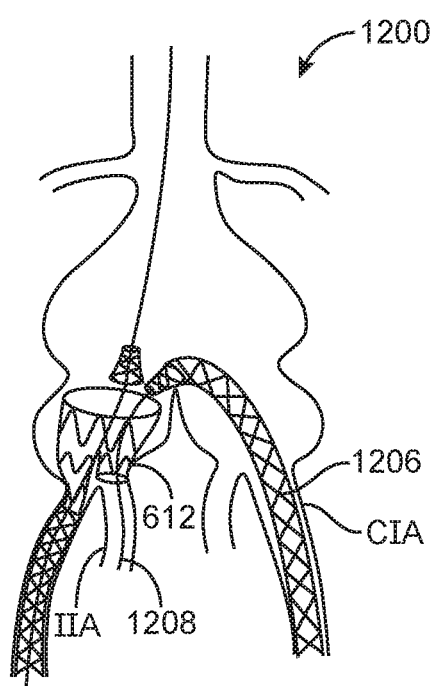

In a third step as shown in FIG. 12C, a delivery system 1206 including branch extension 314 is advanced from the contralateral common iliac artery CIA and over the aortic bifurcation over a guidewire 1208. The delivery system 1206 is advanced through the branch limb 612 into the internal iliac artery IIA. The branch extension 314 is then deployed from the delivery system 1206 and deployment of ABBD 900 is completed as illustrated in a fourth step in FIG. 12D. The branch extension 314 is deployed using a cross-over technique using a steerable catheter such as the steerable catheter 402 and guidewire 402 as described in the embodiments of FIGS. 4-5 and/or using the TnT wire 404. In another embodiment, the branch extension 314 is deployed from supra-aortic access in a manner similar to that illustrated in FIGS. 3E, 3F.

Figure 12D:
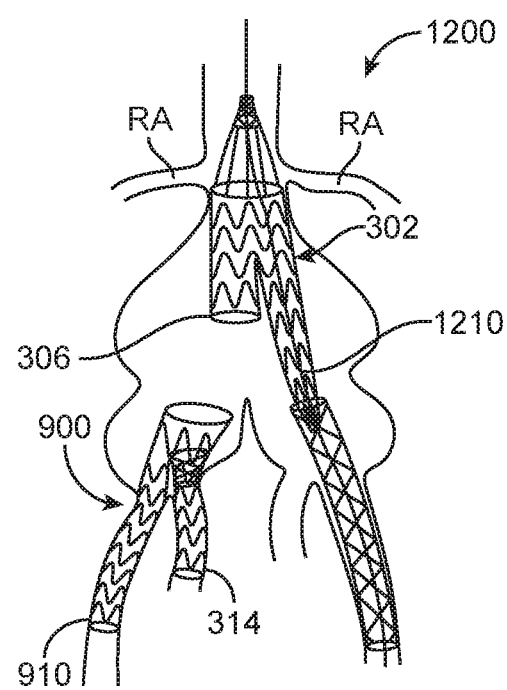

In the fourth step as shown in FIG. 12D, the stent-graft 302 may be deployed in the aorta proximal to the aortic bifurcation. In the example shown, the stent-graft 302 is deployed with its proximal end near the renal arteries RA. In FIG. 12D, the stent-graft 302 is partially deployed, with one branch limb 306 fully deployed and the other branch limb 1210 only partially deployed. In the embodiment shown, the branch limbs 306, 1210 have different length, however they may have the same or similar lengths.

Figure 12E:
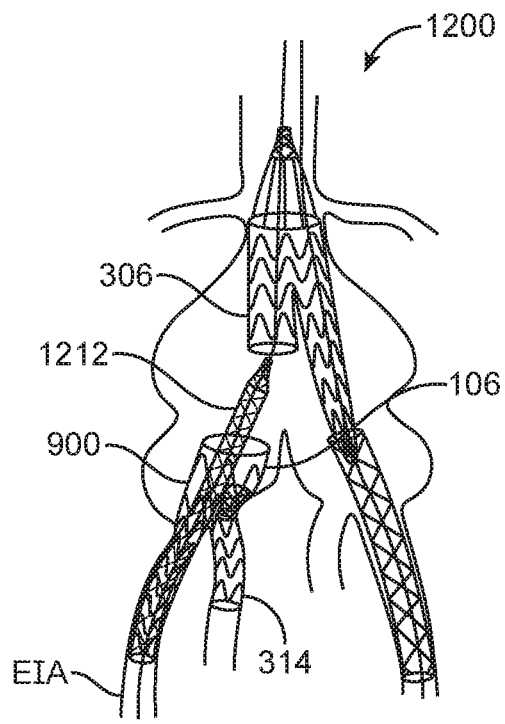
Figure 12F:
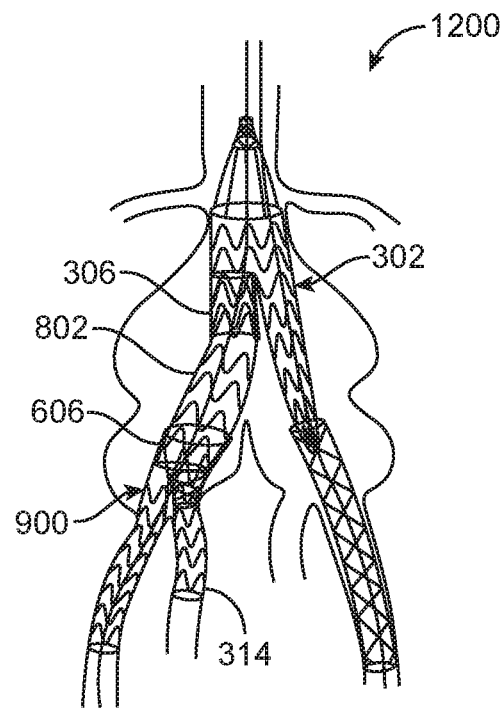
Figure 12G:
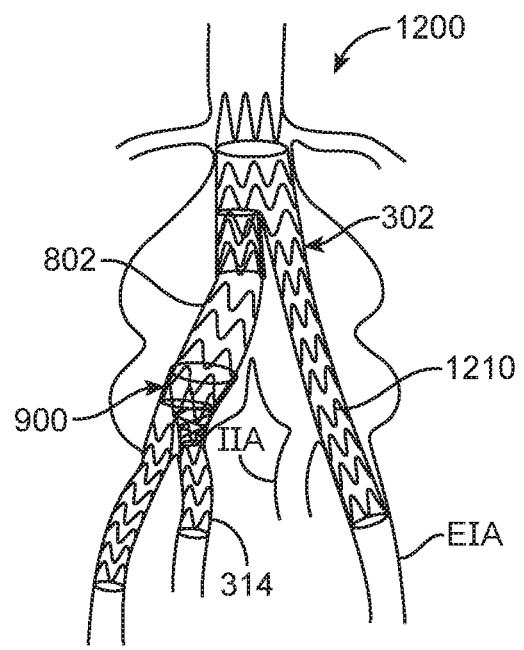

In the fifth step as shown in FIG. 12E, a delivery system 1212 including the branch extension 802 is advanced through the external iliac artery EIA, through ABBD 900, and into branch limb 306. In a sixth step as illustrated in FIG. 12F, the branch extension 802 is deployed within the branch limb 306 of the stent-graft 302 and the body segment 606 of the ABBD 900. Finally, in a seventh step as illustrated in FIG. 12G, deployment of the stent-graft 302 is completed. In this embodiment, the branch limb 1210 of the stent-graft 302 extends directly into the external iliac artery EIA and the internal iliac artery IIA is excluded. If branch limb 1210 does not reach the EIA, a bridging stent graft (or grafts) may be deployed. The embodiments shown and described with reference to FIGS. 12A-G relate to a single or unilateral procedure in which one set of iliac arteries are treated. However, in other embodiments, the procedure may be bilateral, such that both sets of iliac arteries are treated (e.g., as shown in FIGS. 3A-K). One of ordinary skill in the art will understand, based on the present disclosure, that the steps taken on the treated side (left side, as shown) may be repeated on the other side to complete the treatment.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:
1. A method comprising:
 deploying a bifurcated stent-graft within an aorta proximal to an aortic bifurcation;

deploying a body segment of a first bifurcating branch device coupled to a first branch limb of the bifurcated stent-graft;

deploying a first branch extension coupled to a first branch limb of the first bifurcating branch device and within a first vessel; and deploying a second branch extension within a second branch limb of the first bifurcating branch device and within a second vessel, wherein the deploying the second branch extension comprises:

advancing a steerable catheter through a second branch limb of the bifurcated stent-graft;

deflecting a distal tip of the steerable catheter to point into the second branch limb of the first bifurcating branch device;

passing a first guidewire through the steerable catheter and the first branch limb of the first bifurcating branch device to be within the first vessel; and advancing a delivery system comprising the second branch extension over a second guidewire extending through the steerable catheter and the second branch limb of the first bifurcating branch device to be within the second vessel, wherein during the advancing the delivery system, constant tension is maintained on the first guidewire to prevent the steerable catheter from straightening out.

2. The method of claim 1 wherein the first vessel is selected from the group consisting of an external iliac artery and an internal iliac artery.

3. The method of claim 1 wherein the first A-bifurcating branch device further comprises:
an upper segment comprising:
a nonflared portion extending to a proximal end of the bifurcating branch device; and
a flared portion having a greater diameter than the nonflared portion; and
a lower segment comprising:
the first branch limb of the first bifurcating branch device; and
the second branch limb the first bifurcating branch device, wherein the flared portion is located between the nonflared portion and the lower segment, wherein the upper segment, the first branch limb of the first bifurcating branch device, and the second branch limb of the first bifurcating branch device comprises a single integral graft material.

4. The method of claim 3 wherein the first vessel is an external iliac artery.

5. The method of claim 4 wherein the second vessel is an internal iliac artery.

6. The method of claim 1 wherein the bifurcated stent-graft further comprises a body coupled to the first branch limb of the bifurcated stent-graft and to the second branch limb of the bifurcated stent-graft.

7. The method of claim 1 wherein the body segment of the first bifurcating branch device comprises a nonflared portion and a flared portion.

8. The method of claim 7 wherein the nonflared portion extends to a proximal end of the first bifurcating branch device.

9. The method of claim 8 wherein the first bifurcating branch device further comprises a lower segment comprising:
the first branch limb of the first bifurcating branch device; and
the second branch limb of the first bifurcating branch device, wherein the flared portion is between the nonflared portion and the lower segment.

10. The method of claim 9 wherein the body segment, the first branch limb of the first bifurcating branch device, and the second branch limb of the first bifurcating branch device comprises a single integral graft material.

11. The method of claim 7 wherein the flared portion has an increase in diameter between the nonflared portion and the lower segment.

12. The method of claim 1 further comprising deploying a body segment of a second bifurcating branch device coupled to the second branch limb of the bifurcated stent-graft, the second bifurcating branch device comprising:
a first branch limb; and
a second branch limb.

13. The method of claim 12 further comprising:
deploying a third branch extension within the first branch limb of the second bifurcating branch device and within a third vessel.

14. The method of claim 13 further comprising:
deploying a fourth branch extension within the second branch limb of the second bifurcating branch device and within a fourth vessel.

15. The method of claim 1 wherein the first branch limb of the first bifurcating branch device moves independent of the second branch limb of the first bifurcating branch device.

16. The method of claim 1 wherein the body segment of the first bifurcating branch device is coupled to the first branch limb of the bifurcated stent-graft by a branch extension.

17. The method of claim 1 wherein the first branch limb of the first bifurcating branch device has a different length than the second branch limb of the first bifurcating branch device.

18. The method of claim 7 wherein a diameter of the first branch limb of the first bifurcating branch device added to a diameter of the second branch limb of the first bifurcating branch device is greater than a diameter of the nonflared portion.

19. The method of claim 7 wherein a length of the nonflared portion is within a range of 20 to 50 mm, and a diameter of the flared portion is at least 2 mm larger than a diameter of the nonflared portion.

* * * * *